April 16, 1940. J. H. NICOLAS Plant Pat. 374
ROSE PLANT
Filed May 17, 1939
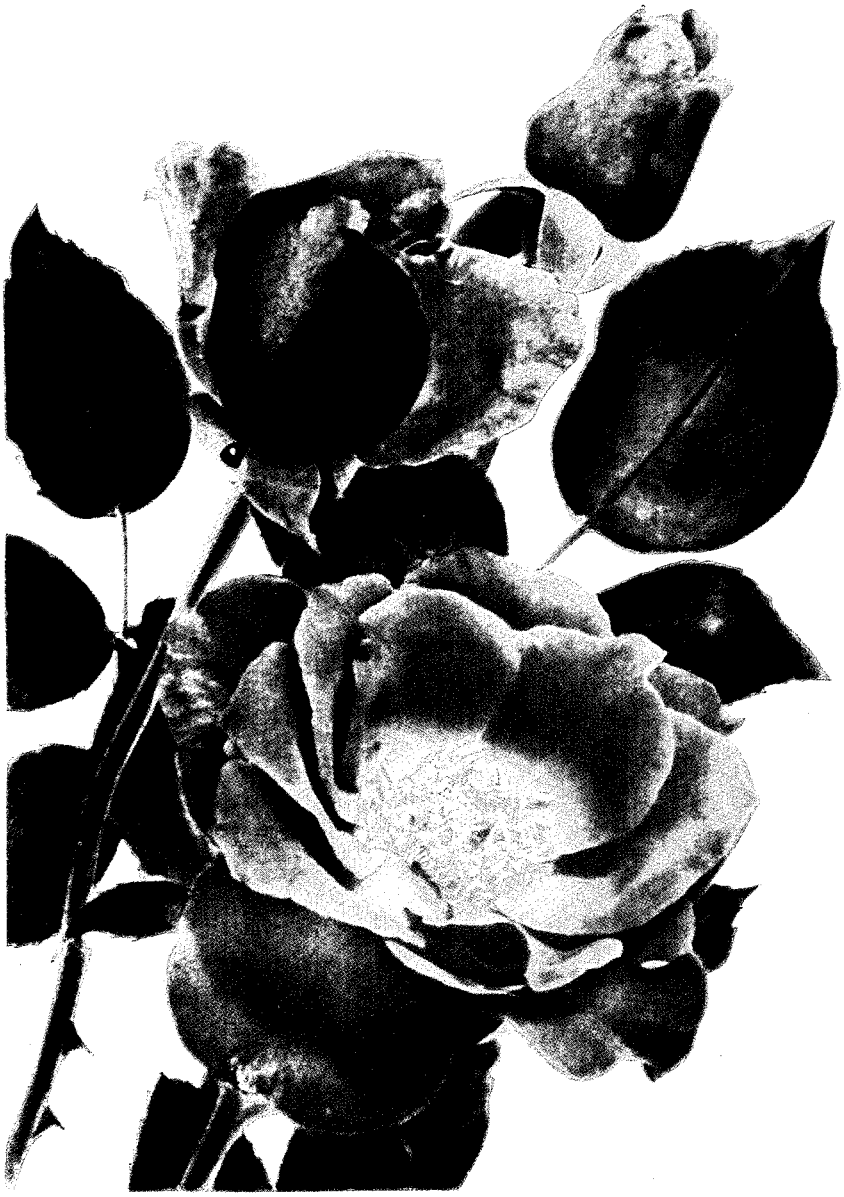
Inventor
Jean H. Nicolas
By Fannie Nicolas
Administratrix of the
Estate of Jean H. Nicolas,
deceased
By Robb & Robb
Attorneys Patented Apr. 16, 1940

Plant Pat. 374

UNITED STATES PATENT OFFICE

374

ROSE PLANT

Jean H. Nicolas, deceased, late of Newark, N. Y., by Fannie Nicolas, administratrix, Newark, N. Y., assignor to Jackson & Perkins Company, Newark, N. Y.

Application May 17, 1939, Serial No. 274,301

1 Claim. (Cl. 47—61)

The present invention relates to a new and distinct variety of Hybrid Tea rose plant, the result of a definite effort to produce an improved rose of distinctive characteristics with respect to its parent.

This new rose originated from a cross of the well known variety Royal Red with Johnizauber which resulted in a rose of novel red coloring, form, and other attractive features. Notably, it will be observed from the accompanying illustration, the bud, when the sepals first divide, is Ox Blood Red, and as the flower half opens, the coloring appears Carmine inside and Ox Blood Red to Carmine outside of the petals. When fully open, the flower is double, high centered with open exposed stamens, and the scalloped edge petals Carmine for the upper two-thirds of the inside shading to Begonia Rose at the bottom and Carmine to Ox Blood Red outside, fading clearly to Spectrum Red at the third day.

Further, the blooms are borne several together on the long, strong stems and last long both as cut flowers and on the bush.

Other features of novelty are set forth in the following detail description of this new variety in which the color terminology is in accord with Ridgway's Color Standard.

Parentage:

*Seed parent.*—Royal Red.

*Pollen parent.*—Johnizauber.

Classification:

*Botanic and commercial.*—Hybrid Tea.

*Flower*

Observations made at Newark, New York, in the morning of June 30, 1938.

Blooming habit:

*Recurrent.*—Continuous.

Bud:

*Size.*—Large.

*Form.*—Long. Is not affected by wet or hot weather.

*Color.*—When sepals first divide—Ox Blood Red, Plate 1. When petals begin to unfurl—Ox Blood Red, Plate 1, to Carmine, Plate 1. When half blown: Inside of petals—Carmine, Plate 1; reverse of petals—Ox Blood Red, Plate 1, to Carmine, Plate 1.

*Sepals.*—Smooth edge. Curl back when half open.

*Calyx.*—Shape—funnel. Size—broad. Aspect—smooth.

*Peduncle.*—Length—long. Aspect—prickly. Color—Cress Green, Plate 31. Strength—stiff, heavy.

*Opening.*—Bud opens well. Is not affected by adverse conditions.

Bloom:

*Size.*—Large. Average size when fully expanded—5″.

*Borne.*—Several together.

*Stems.*—Long, strong.

*Form.*—When first open—flat, high center. Permanence—retains its form to the end exposing full center.

*Petalage.*—Double (full but open center). Number of petals under normal conditions—25.

*Color.*—Center of flower—Carmine upper two-thirds, Plate 1, lightening to Begonia Rose, Plate 1, towards base. Outer petals—Carmine upper two-thirds, Plate 1, lightening to Begonia Rose, Plate 1, towards base. Base of petals (aiglet)—Picric Yellow, Plate 4. Inside of petals—Carmine upper two-thirds, Plate 1, lightening to Begonia Rose, Plate 1, towards base. Reverse of petals—Carmine, Plate 1, to Ox Blood Red, Plate 1. General tonality from a distance—Red (general color terminology).

*Discoloration.*—General tonality at end of first day—Carmine, Plate 1. Second day—Carmine, Plate 1. Third day—Spectrum Red, Plate 1.

Petals:

*Texture.*—Thick. Is not affected by hot or wet weather.

*Appearance.*—Inside—velvety. Outside—satiny.

*Form.*—Scalloped.

*Arrangement.*—Imbricated (regularly arranged shinglelike). Petaloids in center—none.

*Persistence.*—Drop off cleanly.

*Fragrance.*—None. Nature—"Old Rose perfume" (Centifolia).

*Lasting quality.*—On the plant and as cut flower—long.

Genital organs:

*Stamens, anthers.*—Large, many. Color—Cadmium Yellow, Plate 3. Arrangement—regular around styles.

*Stamens, filaments (threads).*—Long. Color—Deep Chrome, Plate 3.

*Pollen.*—Deep Chrome, Plate 3.

*Styles.*—Columnar, even; medium length, heavy.
*Stigmas.*—Empire Yellow, Plate 4.
*Ovaries.*—All enclosed in calyx.
Fruit: Variety is fertile with its own pollen.

*Plant*

Form: Bush.
Growth: Vigorous, upright.
Foliage: 5 to 7 leaflets.
*Size.*—Large.
*Quantity.*—Normal.
*Color.*—New foliage: upper side, center vein—Light Cress Green, Plate 31; balance of leaf—Madder Brown, Plate 13; under side—Madder Brown, Plate 13. Old foliage: upper side—Dark Cress Green, Plate 31; under side—Light Cress Green, Plate 31.
*Shape.*—Oval pointed.
*Texture.*—On upper side and under side—smooth ribs and veins—ordinary.
*Edge.*—Serrated (saw toothed).
*Serration.*—Small.
*Rachis.*—Color—Cress Green, Plate 31, at the bottom, Mineral Red, Plate 27. Under side—Smooth.
*Stipules.*—Medium length, smooth.
*Disease resistance.*—Resistant.

Wood:
*New wood.*—Color—Light Cress Green, Plate 31. Bark—smooth.
*Old wood.*—Color—Cress Green, Plate 31. Bark—Smooth.
Thorns (divided into thorns, prickles and short needles):
*Thorns.*—Quantity: on main stalks from base—few; on laterals from stalk—few. Form—Broad base, short, hooked downward. Color when young—Vandyke Red, Plate 13. Position—irregular.
*Prickles.*—Quantity. On laterals—None.

Asexual reproduction of the plant shows that the distinctive characteristics are established.

What is claimed is:

A new and distinct variety of Hybrid Tea rose plant, characterized as to novelty by the form and distinctive coloring of the flowers in the different stages of their development, the texture and form of the petals of the flowers and the lasting quality as cut flowers and on the bush, substantially as shown and described.

FANNIE NICOLAS.
*Administratrix of the Estate of Jean H. Nicolas, Deceased.*